United States Patent [19]

Lamberti et al.

[11] 3,954,858

[45] May 4, 1976

[54] NOVEL SEQUESTRANT BUILDERS AND METHOD OF MAKING THE SAME

[75] Inventors: Vincent Lamberti, Upper Saddle River; Mark D. Konort, Haworth, both of N.J.; Ira Weil, New York, N.Y.

[73] Assignee: Lever Brothers Company, New York, N.Y.

[22] Filed: July 25, 1972

[21] Appl. No.: 274,954

Related U.S. Application Data

[63] Continuation-in-part of Ser. No. 139,225, April 30, 1971.

[52] U.S. Cl. ............................ 260/535 P; 252/132; 252/142; 252/156; 252/180; 252/545; 252/546; 260/548; 260/429 CY; 260/429.9; 260/439 CY; 260/456 R; 260/458; 260/501.13; 260/526 N; 260/534 E; 260/534 S; 260/526 R

[51] Int. Cl.$^2$.......................................... C07C 59/22

[58] Field of Search................................. 260/535 P

[56] References Cited
UNITED STATES PATENTS

| | | | |
|---|---|---|---|
| 2,098,190 | 11/1937 | Kyrides............................ | 260/484 P |
| 2,281,394 | 4/1942 | Sorenson ......................... | 260/484 P |
| 2,346,612 | 4/1944 | Bothrock......................... | 260/484 P |

OTHER PUBLICATIONS
E. Von Rudloff et al. Canadian J. of Chemistry Vol. 35 pp. 315–321 (1957).

*Primary Examiner*—Anton H. Sutto
*Assistant Examiner*—P. Killos

[57] ABSTRACT

There are disclosed herein novel sequestrant builders for use in detergent compositions having the general formula:

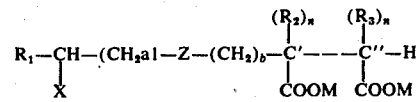

wherein $R_1$ is selected from the group consisting of H, an alkyl group having 1 to 12 carbon atoms, a hydroxylalkyl group having 1 to 4 carbon atoms, and a COOM group; $n$ is zero or 1; when $n$ is 1, $R_2$ and $R_3$ are selected from the group consisting of H, $CH_3$ and $CH_2COOM$; when n is zero a double bond is present between C' and C''; X is COOM, $OSO_3M$ or $SO_3M$; a is zero, 1 or 2; $b$ is zero or 1; Z is selected from the group consisting of O, S, NH, $NR_4$ wherein $R_4$ is an alkyl group or hydroxyalkyl group having 1 to 4 carbon atoms provided that when Z is O, a must be zero, X must be COOM and $R_1$ cannot be H when $R_2$ and $R_3$ are both H and $b$ is zero; M is selected from the group consisting of H, alkali metal, ammonium and substituted ammonium cations.

There is also disclosed herein a novel process for preparing the aforesaid compounds using a novel intramolecular Michael type reaction.

12 Claims, No Drawings

NOVEL SEQUESTRANT BUILDERS AND METHOD OF MAKING THE SAME

This application is a continuation-in-part of an earlier application, Ser. No. 139,225, filed Apr. 30, 1971.

This application is also co-pending with applicant's application Ser. No. 80,166 filed Oct. 12, 1970, now U.S. Pat. No. 3,692,685, which discloses and claims the salts of carboxymethyloxysuccinic acid.

BACKGROUND OF THE INVENTION

1. Field of the Invention

The present invention relates to new sequestrant type builder compounds which do not contain phosphorus and more specifically to detergent compositions containing these new builder compounds. The invention also relates to a novel process for preparing the rather complex compounds by a simple reaction. The sequestrant type builder compounds of the present invention can be generally represented as follows:

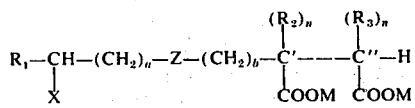

wherein $R_1$ is selected from the group consisting of H, an alkyl group having 1 to 12 carbon atoms, a hydroxyalkyl group having 1 to 4 carbon atoms, and a COOM group; $n$ is zero or 1; when $n$ is 1, $R_2$ and $R_3$ are selected from the group consisting of H, $CH_3$ and $CH_2COOM$; when $n$ is zero a double bond is present between $C'$ and $C''$; X is COOM, $OSO_3M$ or $SO_3M$: $a$ is zero, 1 or 2; $b$ is zero or 1; Z is selected from the group consisting of O, S, NH, $NR_4$ wherein $R_4$ is an alkyl group or hydroxyalkyl group having 1 to 4 carbon atoms provided that when Z is O, $a$ must be zero, X must be COOM and $R_1$ cannot be H when $R_2$ and $R_3$ are both H and $b$ is zero; M is selected from the group consisting of H, alkali metal, ammonium and substituted ammonium cations.

HISTORICAL BACKGROUND OF THE INVENTION AND DESCRIPTION OF THE PRIOR ART

In recent years, studies have been conducted concerning the problems of eutrophication. Eutrophication can be defined as a natural process of enrichment of waters with nutrients, such as phosphorus and nitrogen, at a slow rate Eutrophication can be detrimental, since it may cause increased algal growth and algal scums which are unaesthetic, odorous, distasteful and clog filters of treatment plants. It has been postulated that various human activities have accelerated the process. Contributing factors in the eutrophication of lakes, streams and estuaries are natural runoff, agricultural drainage, ground water, precipitation, sewage and waste effluents. It has been postulated that the phosphorus-containing builders present in detergent compositions can be a factor in eutrophication, and therefore any substitutes which do not contain phosphorus may decrease to some extent the eutrophication problem. Thus, those skilled in the art have expended a great deal of time and money to find suitable materials to reduce or replace the existing phosphate builders in detergent compositions. This work is still continuing and represents a large fraction of the industry's total research and development efforts.

The compounds of the present invention which have been suggested in the prior art are carboxymethylthiosuccinic acid

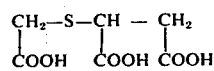

described in The Journal of Organic Chemistry Vol. 27 pages 3140–6 (1962) authored by Zienty et al and carboxymethyloxymethylsuccinic acid

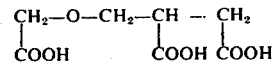

described in The Chemical Abstracts Vol. 49 page 4638 (f) (1955). However, neither of these compounds has been suggested as a builder for use in a detergent composition. The other compounds of the present invention are novel materials which have not been described or suggested in the art.

SUMMARY OF THE INVENTION

It is therefore an object of the present invention to provide novel builder compounds which are free of phosphorus and can be incorporated into detergent compositions.

The compositions of the invention necessarily include both a synthetic builder and a water-soluble organic detergent compound. Such detergent compounds that are useful in the present invention are the anionic (soap and nonsoap), nonionic, zwitterionic and ampholytic compounds. The chemical nature of these detergent compounds is not an essential feature of the present invention. Moreover, such detergent compounds are well known to those skilled in the detergent art and the patent and printed literature are replete with disclosures of such compounds. Typical of such literature are "Surface Active Agents" by Schwartz and Perry and "Surface Active Agents and Detergents" by Schwartz, Perry and Berch, the disclosures of which are incorporated by reference herein.

The phosphorus-free builders for the detergent compositions of the invention are the normal alkali metal, ammonium and substituted ammonium salts of polycarboxylic acids which can be generally represented as follows:

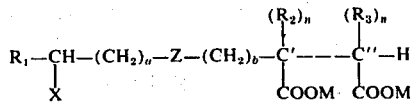

wherein $R_1$ is selected from the group consisting of H, an alkyl group having 1 to 12 carbon atoms, a hydroxyalkyl group having 1 to 4 carbon atoms, and a COOM group; $n$ is zero or 1; when $n$ is 1, $R_2$ and $R_3$ are selected from the group consisting of H, $CH_3$ and $CH_2COOM$; when $n$ is zero a double bond is present between $C'$ and $C''$; X is COOM, $OSO_3M$ or $SO_3M$: $a$ is zero, 1 or 2; $b$ is zero or 1; Z is selected from the group consisting of O, S, NH, $NR_4$ wherein $R_4$ is an alkyl group or hydroxyalkyl group having 1 to 4 carbon atoms provided that when Z is O, $a$ must be zero, X must be COOM and $R_1$ cannot be H when $R_2$ and $R_3$ are both H and $b$ is zero;

M is selected from the group consisting of H, alkali metal, ammonium and substituted ammonium cations.

The substituted ammonium cations are well known to the art and are for example represented by morpholinium, alkyl ammonium, mono-, di-, and trialkanol ammonium and tetra alkyl ammonium.

Of course if no nitrogen is desired in the builder compound, the alkali metal cations should be used.

Typical compounds of the present invention are shown in Table I.

Table I

| | $R_1$ | X | a | Z | b | $R_2$ | $R_3$ | C' & C'' | $R_4$ | Product |
|---|---|---|---|---|---|---|---|---|---|---|
| 1. | $CH_3$ | COOM | 0 | Oxy. | 0 | H | H | Single bond | — | Trisodium Lactoxysuccinate $CH_3CH-O-CH-CH_2$ <br> $\quad\quad\quad\quad\;\;COONa\;\;\;COONa\;\;COONa$ |
| 2. | Polyhydroxyalkyl ($C_4$) | COOM | 0 | Oxy. | 0 | H | H | '' | — | Trisodium 2-Gluconoxysuccinate $CH(OH)CH(OH)CH(OH)CH_2OH$ <br> $CH-O-CH-CH_2$ <br> $COONa\;\;\;\;COONa\;\;COONa$ |
| 3. | H | COOM | 0 | S | 0 | H | H | '' | — | Trisodium Carboxymethylthiosuccinate $CH_2-S-CH-CH_2$ <br> $COONa\;\;\;\;COONa\;\;COONa$ |
| 4. | H | COOM | 0 | NH | 0 | H | H | '' | — | Trisodium Carboxymethylaminosuccinate $CH_2-NH-CH-CH_2$ <br> $COONa\;\;\;\;\;\;COONa\;\;COONa$ |
| 5. | H | COOM | 0 | $NR_4$ | 0 | H | H | '' | $CH_3$ | Trisodium Sarcosinylsuccinate $CH_2-N-CH-CH_2$ <br> $COONa\;CH_3\;COONa\;\;COONa$ |
| 6. | H | COOM | 1 | NH | 0 | H | H | '' | — | Trisodium N-(2-carboxyethyl) aspartate $CH_2CH_2NHCH-CH_2$ <br> $COONa\;\;\;\;COONa\;\;COONa$ |
| 7. | H | $SO_3M$ | 1 | NH | 0 | H | H | '' | — | Trisodium N-(2-sulfoethyl) aspartate $NaO_3S-CH_2CH_2NHCH-CH_2$ <br> $\quad\quad\quad\quad\quad\quad\quad\;\;COONa\;\;COONa$ |
| 8. | H | COOM | 0 | Oxy. | 0 | — | — | Double bond | — | Trisodium carboxymethyloxymaleate $CH_2-O-C=CH$ <br> $COONa\;\;\;\;COONa\;COONa$ |
| 9. | H | COOM | 0 | Oxy. | 0 | H | $CH_2COOM$ | Single bond | — | Tetrasodium α-carboxymethyloxy-β-carboxymethylsuccinate $CH_2-O-CH-CH-CH_2$ <br> $COONa\;\;COONa\;\;COONa\;COONa$ |
| 10. | H | COOM | 0 | NH | 0 | H | $CH_3$ | '' | — | Trisodium α-carboxymethylamino-β-methylsuccinate $NaOOCCH_2-NH-CH-CH-CH_3$ <br> $\quad\quad\quad\quad\quad\quad\;COONa\;\;COONa$ |
| 11. | COOM | COOM | 0 | Oxy. | 0 | H | H | '' | — | Tetrasodium Tartronoxysuccinate $(NaOOC)_2CHOCH-CH_2$ <br> $\quad\quad\quad\quad\quad\;COONa\;\;COONa$ |
| 12. | H | COOM | 0 | Oxy. | 1 | H | H | '' | — | Trisodium Carboxymethyloxymethylsuccinate $CH_2OCH_2CH-CH_2$ <br> $COONa\;\;COONa\;\;COONa$ |
| 13. | H | COOM | 0 | Oxy. | 0 | H | $CH_3$ | '' | — | Trisodium α-carboxymethyloxy-β-methylsuccinate $CH_2-O-CH-CHCH_3$ <br> $COONa\;\;COONa\;\;COONa$ |
| 14. | $CH_3(CH_2)_9$ | COOM | 0 | Oxy. | 0 | H | H | '' | — | Trisodium [(1-carboxy) undecyloxy]succinate $CH_3(CH_2)_9CH-O-CH-CH_2$ <br> $\quad\quad\quad\quad\;COONa\;COONa\;COONa$ |
| 15. | H | COOM | 2 | NH | 0 | H | H | '' | — | Trisodium N(3-carboxypropyl)aspartate $CH_2-(CH_2)_2-NH-CH-CH_2$ <br> $COONa\;\;\;\;\;\;\;\;\;\;\;\;\;\;\;COONa\;COONa$ |
| 16. | H | COOM | 0 | $NR_4$ | 0 | H | H | '' | $CH_2-CH_2OH$ | Trisodium N(2-hydroxyethyl)-N-carboxymethylaspartate $CH_2CH_2OH$ <br> $CH_2-N-CH-CH_2$ <br> $COONa\;\;COONa\;\;COONa$ |
| 17. | $CH_3CH_2CH_2$ | COOM | 0 | Oxy. | 0 | H | H | '' | — | Trisodium[(1-carboxy)butoxy]succinate $CH_2(CH_2)_2CH-O-CH-CH_2$ <br> $\quad\quad\quad\quad\;COONa\;COONa\;COONa$ |
| 18. | H | $OSO_3M$ | 1 | NH | 0 | H | H | '' | — | Trisodium N(2-sulfatoethyl)aspartate $CH_2CH_2NH-CH-CH_2$ <br> $OSO_3Na\;\;\;\;\;COONa\;COONa$ |

The weight ratio of the builder compounds of the present invention to detergent compound when used in laundering and hand dishwashing compositions, ranges generally from about 1:20 to about 20:1. When the novel builders are used in mechanical dishwashing compositions, the ratio of builder to detergent compound is from about 10:1 to about 50:1.

Builder compounds of the present invention can be used either as the sole builder or where desired can be used in conjunction with other builders, examples of which include tetrasodium and tetrapotassium pyrophosphate, pentasodium and pentapotassium tripolyphosphate, trisodium and tripotassium nitrilotriacetate, polyacrylates, ether polycarboxylates, citrates, starch or cellulose derived polycarboxylates, and the like. Other materials which may be present in the detergent compositions of the invention are those conventionally present therein. Typical examples thereof include soil suspending agents, hydrotropes, corrosion inhibitors, dyes, perfumes, fillers, abrasives, optical brighteners, enzymes, suds boosters, suds depressants, germicides, anti-tarnishing agents, cationic detergents, softeners, chlorine releasing agents, buffers and the like. The balance of the detergent compositions is water.

The detergent compositions of the present invention may be in any of the usual physical forms for such compositions, such as powders, beads, flakes, bars, tablets, noodles, liquids, pastes, and the like. The detergent compositions are prepared and utilized in the conventional manner.

When using the detergent compositions of the invention to wash clothes, the wash solutions should have a pH from about 7 to about 12, preferably from about 9 to about 11. Therefore, the presence of a buffer in the detergent composition is usually desirable. Examples of such buffers are sodium silicate, carbonate or bicarbonate.

When the pH value of the wash solution is below about 8.6 some of the salts of the builder compounds will be present in the acid salt form and some in the normal salt form.

It should also be noted that when the compounds of the present invention are employed as the free acids or as partly neutralized salts, the compounds have utility in metal cleaning compositions under pH conditions of about 2 to about 5.

The preferred method for preparing the compounds of the present invention is to react a compound containing both an active hydrogen function e.g. OH, SH, $NH_2$, etc. and a salt forming radical e.g. COOH, $OSO_3H$ and $SO_3H$ with an $\alpha,\beta$-unsaturated polycarboxylic acid. The two reactants are in the form of a mixed alkaline earth metal salt such as the calcium salt. It should be understood that other polyvalent salts can be used such as magnesium, strontium, barium, zinc, iron, manganese, cobalt and the like.

It should also be understood that the process can be used to make not only the compounds of the general formula above but also compounds wherein $R_4$ is $CH_2COOM$ when Z is $NR_4$.

The reaction is carried out in an aqueous medium having a pH of about 8 to about 12.5 and preferably between 11 to 12. The pH of the aqueous medium should be adjusted with an alkaline earth metal reagent such as calcium hydroxide, strontium hydroxide, barium hydroxide and the like, as well as the corresponding oxides. If desired an alkali metal hydroxide can be used to adjust the pH of the medium provided the alkaline earth metal reagent is also present.

It has also been found that when using relatively insoluble alkaline earth metal hydroxides such as magnesium hydroxide, the initial pH at room temperature of the reaction mixture even with an excess amount of the hydroxide is only about 8 to 9. However, by heating the reaction mixture at reflux temperatures or heating at superatmospheric pressure satisfactory yields of the product can be obtained.

The mole ratio of the compound containing the active hydrogen and salt forming radical hereinafter referred to as the active hydrogen compound and the $\alpha,\beta$-unsaturated polycarboxylic acid, hereinafter referred to as the unsaturated acid, is from about 1:1 to about 2:1. The concentrations of the active hydrogen compound and the unsaturated acid are not critical to the invention although it is preferred to use concentrations from about 0.5 molar to about 5 molar in the mixed salt species. It has been found that the higher concentrations increase the rate of reaction.

The temperature at which the reaction may be carried out is normal reflux temperature (100°–102° C) or below reflux temperature say, 60° C. However, if the reaction is carried out at temperatures above reflux temperature, 102°–200° C, the rate of reaction is increased so that at certain elevated temperatures the reaction may be completed within a very short time.

While the entire mechanism of the reaction is not completely understood it is believed that the reaction involves an intramolecular base-catalyzed Michael type reaction.

More specifically the present reaction differs from the Michael reaction in that the present reaction involves intramolecular addition of a nucleophilic species across an $\alpha,\beta$-unsaturated system. The Michael reaction is generally an intermolecular reaction which involves a carbanion and is usually carried out in anhydrous organic solvents. Also the present reaction is believed to involve alkoxide ions, mercaptide ions or amine groups and is carried out in an aqueous medium.

The mixed polyvalent salt is believed to be critical to the reaction in that it brings and holds the reacting sites of the compounds in close proximity to achieve an intramolecular addition. In fact, when the active hydrogen function is hydroxyl, the reaction does not occur in aqueous solutions at all in the absence of a polyvalent metal ion even at high pH.

It is believed that the reaction proceeds in the following manner for the case where the active hydrogen function is the hydroxyl group.

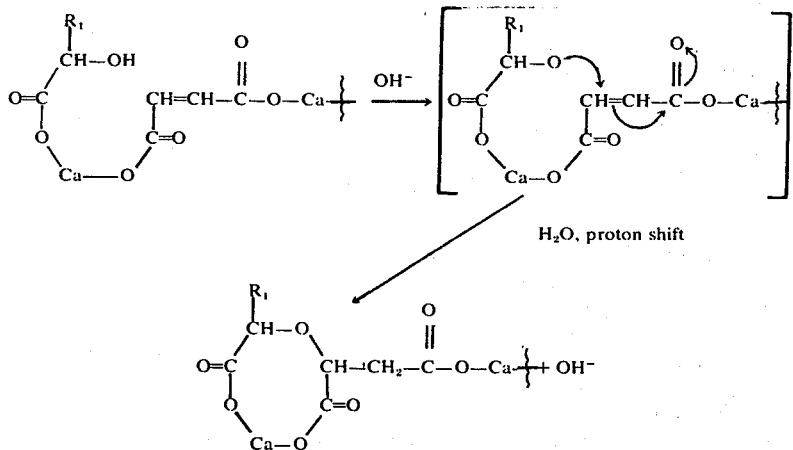

Similarly, when the hydrogen function is a mercapto group, the reaction is believed to proceed in a similar manner except that a mercaptide ion (—S⁻) is involved instead of an alkoxide ion.

When the active hydrogen function is the amino group the reaction is believed to proceed as follows:

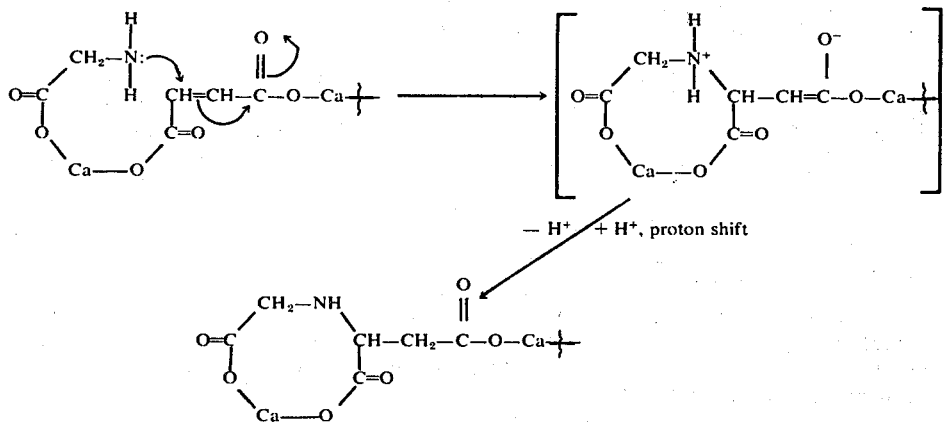

An interesting intermediate product formed during the process is the polyvalent chelate salt of the reaction product.

This salt can involve either two or more molecules of the reaction product and generally can be readily isolated from the reaction mixture because of its low solubility. In some cases the polyvalent chelate salt of the reaction product is very soluble such as in the case of lactoxysuccinate. In this case, if it is desirable to isolate the polyvalent salt, standard methods such as precipitation with an organic solvent such as ethanol, methanol or acetone are used. The conventional monochelate salt involving only one molecule of the reaction product, which is soluble, may be obtained by either partially or totally cation-exchanging the chelate salt with protons followed by neutralization with the appropriate polyvalent metal hydroxide or polyvalent metal hydroxide and alkali metal hydroxide. For purposes of convenience, hereinafter the several types of alkaline earth metal or polyvalent metal chelate salts will be referred to as simply polyvalent salts of the reaction product. Examples of the polyvalent salts are monosodium calcium lactoxysuccinate,

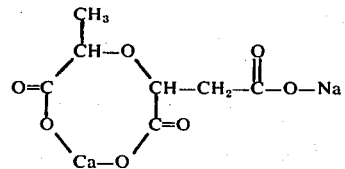

calcium hydrogen lactoxysuccinate,

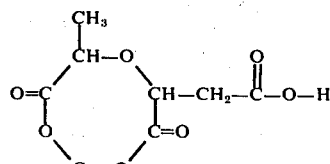

and tricalcium bis(lactoxysuccinate)

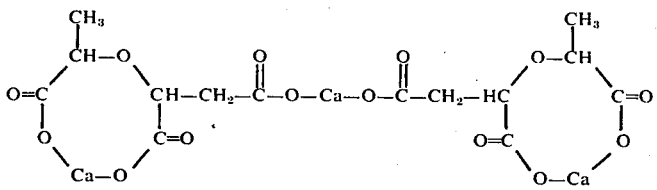

It is to be understood that the particular cation used will determine the particular polyvalent salt. It will also be appreciated that the calcium chelate salts have utility as an animal feed, plate nutrient or in any other area requiring calcium. Of course, other alkaline earth metal salts and other polyvalent salts such as zinc, iron, manganese, cobalt and the like could also be formed and used for the same or similar purposes.

While the alkali metal, ammonium and substituted ammonium salts of the compounds of the invention are useful as builders, they are also effective as boiler scale removers, degreasers, and rust and stain removers. The acid forms are particularly effective rust removers.

The following examples will illustrate further the present invention without, however, limiting the same thereto. All percentages in the examples are by weight.

GENERAL REACTION PROCEDURE

An $\alpha,\beta$-unsaturated carboxylic acid, 0.20 mole, is dissolved in 200 ml. water. If the $\alpha,\beta$-unsaturated carboxylic acid is in the anhydride form, the mixture is stirred for 10–15 minutes to convert the anhydride to the acid. Then 0.20 to 0.24 mole of the active hydrogen compound containing a salt-forming radical, preferably in its acid form, is added. Next, sufficient calcium hydroxide is added to neutralize all acidic groups and bring the pH to about 8–12.5 as measured initially at room temperature. The reaction mixture is then refluxed from about one to eight hours (conversion to product is followed by NMR analysis of a decalcified sample of the reaction mixture). After cooling the reaction mixture to 60° C, 10% excess sodium carbonate (based on the $Ca(OH)_2$ used) is added and the mixture stirred for 10–15 minutes. The precipitated calcium carbonate is filtered and the filtrate, after adjustment of pH to 8.6 with dilute sulfuric acid or by use of a cation exchange resin, is evaporated to dryness to give the product. Analysis of the product, where possible, is carried out by NMR using an internal standard of potassium biphthalate and an external standard of tetramethylsilane. The products may be purified further, if desired, by recrystallization from aqueous ethanol or by precipitation from water with ethanol. Excess carbonate can be removed by first acidifying, preferably with a cation exchange resin, to liberate $CO_2$ followed by neutralization to the required pH with the desired base to reform the salt which is readily isolated by filtration of the resin and evaporation of the filtrate.

When the potassium or lithium salts are desired the corresponding carbonates are used in place of sodium carbonate. When ammonium or substituted ammonium salts are desired, the product obtained from the preparation utilizing an alkali metal carbonate is subsequently cation exchanged with protons followed by neutralization with the appropriate alkaline reagent e.g. ammonium hydroxide.

The compounds in the following examples are prepared by using the general procedure described above and show the reactants, the reflux time as well as any special reaction conditions.

In the case of the compound of Example 7, the general procedure is modified as follows.

After refluxing, the reaction mixture is filtered hot to remove insoluble calcium taurate. The filtrate is allowed to cool whereupon the pure calcium salt of the desired product precipitates out. The calcium salt is then decomposed by slurrying in water and adding 10% excess sodium carbonate (based on calcium present). The $CaCO_3$ is filtered off and the solution acidified by slurrying with a cation exchange resin to decompose excess carbonate. With the ion exchange resin still present, dilute sodium hydroxide is added until the pH of the supernatant solution is 10.5. The residue is then filtered off and filtrate evaporated to give a residue containing 88% trisodium N-(2-sulfoethyl)aspartate (by NMR).

In the cases where $R_1$ of the general formula above is a substituent other than H and Z is oxygen such as in the case of lactoxysuccinate, the reaction time can be greatly reduced by operating the process at the higher end of the preferred pH range, say pH 12. For example, in the case of lactoxysuccinate when the reaction was run at pH 12 and refluxed at 100° C, a reaction time of one hour was sufficient.

Examples 1–18

| Ex. | Active Hydrogen/ Salt forming Radical Compound | $\alpha,\beta$-Unsaturated Carboxylic Acid or Anhydride | Reflux Time, Hours | Product |
|---|---|---|---|---|
| 1 | lactic acid | maleic anhydride | 7 | Trisodium Lactoxysuccinate<br>$CH_3CH-O-CH----CH_2$<br>$\quad\quad\;\;\;\;\|\quad\quad\;\;\;\|\quad\quad\quad\;\;\|$<br>$\quad\quad\;\;\;COONa\;\;COONa\;\;COONa$ |
| 2 | gluconic acid | maleic anhydride | 5 | Trisodium 2-Gluconoxysuccinate<br>$CH(OH)CH(OH)CH(OH)CH_2OH$<br>$CH-O-CH----CH_2$<br>$\;\|\quad\quad\;\;\|\quad\quad\quad\;\;\|$<br>$COONa\;\;COONa\;\;COONa$ |
| 3 | mercaptoacetic acid | maleic anhydride | 6 | Trisodium Carboxymethyl-thiosuccinate<br>$CH_2-S-CH----CH_2$<br>$\;\;\|\quad\quad\;\;\|\quad\quad\quad\;\;\|$<br>$COONa\;\;COONa\;\;COONa$ |
| 4 | glycine | maleic anhydride | 4 | Trisodium Carboxymethyl aminosuccinate<br>$CH_2-NH-CH----CH_2$<br>$\;\;\|\quad\quad\quad\;\;\|\quad\quad\quad\;\;\|$<br>$COONa\;\;\;\;\;COONa\;\;COONa$ |
| 5 | Sarcosine | maleic anhydride | 4<br>(130°C; pressure reaction) | Trisodium Sarcosinylsuccinate<br>$CH_2----N---CH----CH_2$<br>$\;\;\|\quad\quad\quad\;\;\|\quad\quad\;\;\|\quad\quad\;\;\|$<br>$COONa\;\;CH_3\;\;COONa\;\;COONa$ |

Examples 1–18-continued

| Ex. | Active Hydrogen/ Salt forming Radical Compound | α,β-Unsaturated Carboxylic Acid or Anhydride | Reflux Time, Hours | Product |
|---|---|---|---|---|
| 6 | β-alanine | maleic anhydride | 7 | Trisodium N-(2-carboxyethyl) aspartate<br>CH$_2$CH$_2$NHCH————CH$_2$<br>\|         \|      \|<br>COONa  COONa  COONa |
| 7 | taurine | maleic anhydride | 8 | Trisodium N-(2-sulfoethyl) aspartate<br>NaO$_3$S—CH$_2$CH$_2$NHCH————CH$_2$<br>\|      \|<br>COONa  COONa |
| 8 | glycolic acid | acetylene dicarboxylic acid | 1.5 | Trisodium carboxymethyl-oxymaleate<br>CH$_2$—O—C = CH<br>\|        \|    \|<br>COONa  COONa COONa |
| 9 | glycolic acid | aconitic acid | 5 | Tetrasodium α-carboxymethyloxy-β-carboxymethylsuccinate<br>CH$_2$—O—CH————CH————CH$_2$<br>\|       \|      \|      \|<br>COONa  COONa  COONa  COONa |
| 10 | glycine | citraconic anhydride | 4 | Trisodium α-carboxymethylamino-β-methylsuccinate<br>NaOOCCH$_2$—NH—CH————CH—CH$_3$<br>\|      \|<br>COONa  COONa |
| 11 | tartonic acid | maleic anhydride | 11 | Tetrasodium Tartron-oxysuccinate<br>(NaOOC)$_2$CHOCH————CH$_2$<br>\|      \|<br>COONa  COONa |
| 12 | glycolic acid | itaconic anhydride | 8 | Trisodium Carboxy-methyloxymethylsuccinate<br>CH$_2$OCH$_2$CH————CH$_2$<br>\|       \|      \|<br>COONa  COONa  COONa |
| 13 | glycolic acid | citraconic anhydride | 4 (140°C; pressure reaction) | Trisodium α-carboxy-methyloxy-β-methylsuccinate<br>CH$_2$—O—CH———— CHCH$_3$<br>\|       \|      \|<br>COONa  COONa  COONa |
| 14 | 2-hydroxydodecanoic acid | maleic anhydride | 4 | Trisodium [(1-carboxy)-undecyloxy]succinate<br>CH$_3$(CH$_2$)$_9$CH—O—CH————CH$_2$<br>\|      \|      \|<br>COONa  COONa  COONa |
| 15 | γ-aminopropionic acid | maleic anhydride | 4 | Trisodium N(3-carboxy-propyl) aspartate<br>CH$_2$—(CH$_2$)$_2$—NH—CH————CH$_2$<br>\|                \|      \|<br>COONa           COONa  COONa |
| 16 | N(hydroxyethyl)glycine | maleic anhydride | 4 | Trisodium N(2-hydroxyethyl)-N-carboxymethylaspartate<br>CH$_2$CH$_2$OH<br>\|<br>CH$_2$—N—CH————CH$_2$<br>\|      \|      \|<br>COONa  COONa  COONa |
| 17 | α-hydroxyvaleric acid | maleic anhydride | 1.5 | Trisodium[(1-carboxy)butoxy]-succinate<br>CH$_3$(CH$_2$)$_2$CH—O—CH————CH$_2$<br>\|      \|      \|<br>COONa  COONa  COONa |
| 18 | 2-aminoethylsulfuric acid | maleic anhydride | 4 | Trisodium N(2-sulfatoethyl)-aspartate<br>CH$_2$CH$_2$NH—CH————CH$_2$<br>\|              \|      \|<br>OSO$_3$Na      COONa  COONa |

EXAMPLES 19–93

The detergent formulations set forth in Examples 19–93 below are prepared by blending together the recited components and are then tested for detergency or cleansing ability in the Terg-O-Tometer Test wherein the washing conditions are as follows: 65% Dacron-35% cotton VCD (vacuum cleaner dust) cloth; 120° F; 180 ppm water (2/1 Ca$^{++}$/Mg$^{++}$); 0.2% concentration of the total formulation in the washing solution; pH 10.0. (The pH of the washing solutions given herein was adjusted, where necessary, by the addition of caustic (NaOH) or sulfuric acid thereto).

The average detergency units (DU) of the formulations is the final reflectance of the washed cloth minus the initial reflectance of the soiled cloth (the average of two runs), the reflectance being measured with a Gardner Automatic Color Difference Meter, Model AC–3.

The following abbreviations have been used in the tables and examples: LAS is an anionic surfactant which is sodium linear secondary alkyl (C$_{10}$-C$_{15}$) benzene sulfonate; Neodol 45-11 is a nonionic surfactant which is an adduct of a modified Oxo type C$_{14}$-C$_{15}$ alcohol with an average of 11 moles of ethylene oxide; $C_{14}$-$C_{16}$ HAMT is an ampholytic surfactant which is sodium hydroxyalkyl ($C_{14}$-$C_{16}$) N-methyltaurate; DCH sulfobetaine is a zwitterionic surfactant which is cocodimethylsulfopropyl betaine; STPP is pentasodium tripolyphosphate; RU silicate is a sodium silicate having a $SiO_2$ : $Na_2O$ ratio of 2.4 : 1; DU is detergency units; and bal is balance.

Examples 19–34

Washing Conditions: Terg-O-Tometer; Dacron/Cotton VCD Cloth; 120°F; 180 ppm (2:1 $Ca^{++}/Mg^{++}$) water; pH = 10; formulation concentration, 0.2%

| Component | Formulation (%) | | | | | | | | | | | | | | | |
|---|---|---|---|---|---|---|---|---|---|---|---|---|---|---|---|---|
| | 19 | 20 | 21 | 22 | 23 | 24 | 25 | 26 | 27 | 28 | 29 | 30 | 31 | 32 | 33 | 34 |
| 1. Compound of Example 1 | 50 | | | | | | | | | | | | | | | |
| 2. Compound of Example 2 | | 50 | | | | | | | | | | | | | | |
| 3. Compound of Example 3 | | | 50 | | | | | | | | | | | | | |
| 4. Compound of Example 4 | | | | | | 50 | | | | | | | | | | |
| 5. Compound of Example 5 | | | | | | | | | 50 | | | | | | | |
| 6. Compound of Example 6 | | | | | | | | | | | 50 | | | | | |
| 7. Compound of Example 7 | | | | | | | | | | | | | 50 | | | |
| 8. Compound of Example 8 | | | | | | | | | | | | | | | 50 | |
| 9. STPP | | 50 | | 50 | | 50 | | 50 | | 50 | | 50 | | 50 | | 50 |
| 10. RU Silicate Solids | 10 | 10 | 10 | 10 | 10 | 10 | 10 | 10 | 10 | 10 | 10 | 10 | 10 | 10 | 10 | 10 |
| 11. LAS | 18 | 18 | 18 | 18 | 18 | 18 | 18 | 18 | 18 | 18 | 18 | 18 | 18 | 18 | 18 | 18 |
| 12. Water | | | | | | | | bal. | | | | | | | | |
| Average Detergency Units (DU's) | 22.1 | 29.4 | 23.1 | 28.9 | 18.7 | 27.0 | 25.6 | 26.8 | 27.4 | 28.7 | 26.3 | 28.4 | 12.6 | 29.1 | 27.2 | 28.8 |

EXAMPLES 34–44

Separate detergent formulations having the recited components of Example 19 are prepared except that each of the compounds of Examples 9 through 18 inclusive are substituted in place of the compound of Example 1. Each of the detergent formulations are then tested for cleansing ability in the Terg-O-Tometer Test described above. It is found that each of the compounds of Examples 9–18 have acceptable building properties.

EXAMPLES 45–93

Examples 19 through 34 inclusive are repeated except Neodol 45-11, HAMT and DCH sulfobetaine is substituted for LAS.

The detergency building properties with the aforesaid detergent compounds are found to be comparable to the detergency building properties when LAS is used.

EXAMPLES 94–95

Detergency Building Properties of Trisodium Lactoxysuccinate With LAS

Washing Conditions: same as for previous examples.

| | Formulation (%) | |
|---|---|---|
| | 94 | 95 |
| Recrystallized Trisodium Lactoxysuccinate | 50 | — |
| STPP | — | 50 |
| RU Silicate Solids | 10 | 10 |
| LAS | 18 | 18 |
| Water | bal. | bal. |
| Average Detergency Units (DU's) | 31.1 | 31.9 |

It should be pointed out that Examples 94 and 95 are a repeat of Examples 19 and 20 shown above except that a purified sample of trisodium lactoxysuccinate was used.

Examples 96–105

Detergency Building Properties of Trisodium Lactoxysuccinate With Various Surfactants
Washing Conditions: Same as for previous examples.

| Component | Formulation (%) | | | | | | | | | |
|---|---|---|---|---|---|---|---|---|---|---|
| | 96 | 97 | 98 | 99 | 100 | 101 | 102 | 103 | 104 | 105 |
| $Na_3$ Lactoxysuccinate | 50 | — | 50 | — | 50 | — | 50 | — | 50 | — |
| STPP | — | 50 | — | 50 | — | 50 | — | 50 | — | 50 |
| RU Silicate Solids | 10 | 10 | 10 | 10 | 10 | 10 | 10 | 10 | 10 | 10 |
| LAS | 18 | 18 | — | — | — | — | — | — | — | — |
| $C_{15-18}$ AOS[a] | — | — | 18 | 18 | — | — | — | — | — | — |
| $C_{14-16}$ HAMT | — | — | — | — | 18 | 18 | — | — | — | — |
| Sulfobetaine DCH | — | — | — | — | — | — | 18 | 18 | — | — |
| Tergitol 15-S-7[b] | — | — | — | — | — | — | — | — | 20 | 20 |
| Water | | | | | bal. | | | | | |
| Average Detergency Units (DU's) | 22.1 | 18.7 | 13.1 | 14.7 | 11.7 | 13.4 | 17.1 | 18.5 | 21.4 | 21.6 |

[a] =sodium $C_{15}$-$C_{18}$ α-olefin sulfonate
[b] =the reaction product of seven moles of ethylene oxide with one mole of linear $C_{11}$-$C_{15}$ random secondary alcohols derived from $C_{11}$-$C_{15}$ normal paraffins.

It is of course understood and appreciated that most of the compounds of the present invention form hydrates in isolatable form. For example, trisodium lactoxysuccinate forms a trihydrate when crystallized from a mixture of ethanol and water. The trihydrate shows a transition peak at 135° C by Differential Thermal Analysis. Thus, when the compounds were named heretofore and in the claims, it is intended to include all hydrate forms as well as the anhydrous forms of such compounds.

It is also to be understood that the compounds of the invention contain one or more asymmetric centers and can therefore exist in more than one stereoisomeric form. Thus, in the case of trisodium lactoxysuccinate two asymmetric centers are present and, therefore, the compound can exist as two optically inactive racemates which may be designated as $dl$ and $d'l'$, and as the optical active isomers $d$, $l$, $d'$ and $l'$. In preparing lactoxysuccinate, either racemic (inactive) lactic acid, (+) lactic acid, (−) lactic acid or mixtures thereof may be used to produce a mixture of stereoisomeric lactoxysuccinates. Thus when the compounds were named heretofore and in the claims, it is intended to include all stereoisomeric forms and mixtures thereof.

It is further intended to cover all changes and modifications of the preferred embodiments of the invention, herein chosen for the purpose of illustration, which do not constitute departures from the spirit and scope of the invention.

What is claimed is:

1. A compound having the general formula:

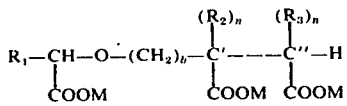

wherein $R_1$ is selected from the group consisting of H, an alkyl group having 1 to 12 carbon atoms; a hydroxyalkyl group having 1 to 4 carbon atoms, and a COOM group; $n$ is zero or 1; when $n$ is 1, $R_2$ and $R_3$ are selected from the group consisting of H, $CH_3$ and $CH_2COOM$ provided that when $R_1$ is H, $R_2$ and $R_3$ cannot both be H; when $n$ is zero a double bond is present between C' and C''; $b$ is zero or 1 and M is selected from the group consisting of H, alkali metal, ammonium and substituted ammonium cations.

2. A compound of claim 1 wherein $n = 1$, $R_2 = H$ and $R_3$ is selected from the group: $CH_3$ and $CH_2COOM$.

3. The compound of claim 1 which is carboxymethyloxymaleic acid and the salts thereof.

4. The compound of claim 1 which is lactoxysuccinic acid and the salts thereof.

5. The compound of claim 1 which is α-carboxymethyl-β-methylsuccinic acid and the salts thereof.

6. Monosodium calcium lactoxysuccinate.

7. Calcium hydrogen lactoxysuccinate.

8. Tricalcium bis(lactoxysuccinate).

9. A process for the preparation of the salts of compounds having the general formula:

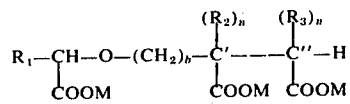

wherein $R_1$ is selected from the group consisting of H, an alkyl group having 1 to 12 carbon atoms, a hydroxyalkyl group having 1 to 4 carbon atoms, and a COOM group, $n$ is zero or 1; when $n$ is 1, $R_2$ and $R_3$ are selected from the group consisting of H, $CH_3$ and $CH_2COOM$; when $n$ is zero a double bond is present between C' and C''; and $b$ is zero or 1 provided $R_1$ cannot be H when $R_2$ and $R_3$ are H and $b$ is zero; M is selected from the group consisting of H, alkali metal, ammonium, and substituted ammonium cations, comprising the steps of:

i. forming a mixed salt of an active hydrogen compound wherein the active hydrogen is a hydroxyl group and an αβ-unsaturated carboxylic acid by reacting said active hydrogen compound and said unsaturated carboxylic acid in an aqueous medium with a compound selected from the group consisting of zinc hydroxide, zinc oxide, alkaline earth metal hydroxides, alkaline earth metal oxides and mixtures thereof at a pH of about 8.0 to about b 12.5 as measured at about 25° C, ii. heating said mixed salt to form a reaction mixture containing the zinc or alkaline earth metal salts of the compounds of the general formula, and iii. treating said reaction mixture in order to substitute alkali metal, ammonium or substituted ammonium cations for the zinc or alkaline earth metal cations to form the alkali metal, ammonium or substituted ammonium salts of the compounds of the general formula.

10. The process of claim 9 wherein heating of the mixed salts is carried out at temperatures from about 100° C to about 200° C.

11. The process of claim 9 wherein the compound selected from the group consisting of zinc hydroxide, zinc oxide, alkaline earth metal hydroxides, alkaline earth metal oxides and mixtures thereof is calcium hydroxide.

12. The process of claim 9 wherein the compound selected from the group consisting of zinc hydroxide, zinc oxide, alkaline earth metal hydroxides, alkaline earth metal oxides and mixtures thereof is calcium oxide.

* * * * *